(12) United States Patent
Kohler et al.

(10) Patent No.: US 6,949,118 B2
(45) Date of Patent: Sep. 27, 2005

(54) ENCASED IMPLANT AND METHODS

(75) Inventors: Robert Edward Kohler, Lake Elmo, MN (US); David H. Mowry, Waconia, MN (US)

(73) Assignee: Percardia, Inc., Merrimack, NH (US)

( * ) Notice: Subject to any disclaimer, the term of this patent is extended or adjusted under 35 U.S.C. 154(b) by 279 days.

(21) Appl. No.: 10/052,156

(22) Filed: Jan. 16, 2002

(65) Prior Publication Data

US 2003/0135260 A1 Jul. 17, 2003

(51) Int. Cl.$^7$ .................................. A61F 2/06
(52) U.S. Cl. .................................... 623/1.13
(58) Field of Search ................... 623/1.12–1.13, 623/1.1, 1.15, 1.16, 1.25, 1.3, 1.32, 1.35, 23.7, 23.68; 606/151–153

(56) References Cited

U.S. PATENT DOCUMENTS

| | | |
|---|---|---|
| 4,953,553 A | 9/1990 | Tremulis |
| 5,193,546 A | 3/1993 | Shaknovich |
| 5,258,008 A | 11/1993 | Wilk |
| 5,287,861 A | 2/1994 | Wilk |
| 5,330,486 A | 7/1994 | Wilk |
| 5,344,426 A | 9/1994 | Lau et al. |
| 5,389,096 A | 2/1995 | Aita et al. |
| 5,409,019 A | 4/1995 | Wilk |
| 5,429,144 A | 7/1995 | Wilk |
| 5,470,320 A | 11/1995 | Tiefenbrun et al. |
| 5,554,119 A | 9/1996 | Harrison et al. |
| 5,593,434 A | 1/1997 | Williams |
| 5,618,299 A | 4/1997 | Khosravi et al. |
| 5,662,124 A | 9/1997 | Wilk |
| 5,733,267 A | 3/1998 | Del Toro |
| 5,755,682 A | 5/1998 | Knudson et al. |
| 5,758,663 A | 6/1998 | Wilk et al. |
| 5,807,384 A | 9/1998 | Mueller |
| 5,810,836 A | 9/1998 | Hussein et al. |
| 5,824,071 A | 10/1998 | Nelson et al. |
| 5,830,222 A | 11/1998 | Makower |
| 5,876,373 A | 3/1999 | Giba et al. |
| 5,878,751 A | 3/1999 | Hussein et al. |
| 5,885,259 A | 3/1999 | Berg |
| 5,908,028 A | 6/1999 | Wilk |
| 5,908,029 A | 6/1999 | Knudson et al. |
| 5,922,022 A | 7/1999 | Nash et al. |
| 5,925,012 A | 7/1999 | Murphy-Chutorian et al. |
| 5,931,848 A | 8/1999 | Saadat |
| 5,935,161 A | 8/1999 | Robinson et al. |
| 5,938,632 A | 8/1999 | Ellis |
| 5,944,019 A | 8/1999 | Knudson et al. |
| 5,968,064 A | 10/1999 | Selmon et al. |

(Continued)

FOREIGN PATENT DOCUMENTS

| | | |
|---|---|---|
| AU | 757647 | 2/2003 |
| WO | WO 96/32972 | 10/1996 |

(Continued)

OTHER PUBLICATIONS

US 6,331,185, 12/2001, Gambale et al. (withdrawn)
Tweden et al. *Ventriculocoronary Artery Bypass (VCAB), a Novel Approach to Myocardial Revascularization.*

(Continued)

*Primary Examiner*—(Jackie) Tan-Uyen T. Ho
(74) *Attorney, Agent, or Firm*—Finnegan, Henderson, Farabow, Garrett & Dunner LLP (57) ABSTRACT

A vascular implant includes a scaffold and a tubing in covering relating to the scaffold. Preferably, the tubing completely covers or encases the scaffold interior surface and exterior surface to leave no portion of the scaffold exposed. Methods for constructing includes pulling tubing through a scaffold and folding at least a portion of the tubing over at least one of the ends of the scaffold. Methods for using an implant include performing coronary vessel bypass procedures or forming blood flow paths in a blood vessel utilizing constructions described herein.

17 Claims, 4 Drawing Sheets

U.S. PATENT DOCUMENTS

| | | |
|---|---|---|
| 5,971,993 A | 10/1999 | Hussein et al. |
| 5,976,155 A | 11/1999 | Foreman et al. |
| 5,980,533 A | 11/1999 | Holman |
| 5,980,548 A | 11/1999 | Evans et al. |
| 5,984,956 A | 11/1999 | Tweden et al. |
| 5,990,379 A * | 11/1999 | Gregory .................. 128/898 |
| 5,997,525 A | 12/1999 | March et al. |
| 5,999,678 A | 12/1999 | Murphy-Chutorian et al. |
| 6,004,261 A | 12/1999 | Sinofsky et al. |
| 6,004,347 A | 12/1999 | McNamara et al. |
| 6,007,543 A | 12/1999 | Ellis et al. |
| 6,010,449 A | 1/2000 | Selmon et al. |
| 6,026,814 A | 2/2000 | LaFontaine et al. |
| 6,029,672 A | 2/2000 | Vanney et al. |
| 6,035,856 A | 3/2000 | LaFontaine et al. |
| 6,036,677 A | 3/2000 | Javier, Jr. et al. |
| 6,036,697 A | 3/2000 | DiCaprio |
| 6,045,565 A | 4/2000 | Ellis et al. |
| 6,053,924 A | 4/2000 | Hussein |
| 6,053,942 A | 4/2000 | Eno et al. |
| 6,056,743 A | 5/2000 | Ellis et al. |
| 6,067,988 A | 5/2000 | Mueller |
| 6,068,638 A | 5/2000 | Makower |
| 6,071,292 A | 6/2000 | Makower et al. |
| 6,076,529 A | 6/2000 | Vanney et al. |
| 6,080,163 A | 6/2000 | Hussein et al. |
| 6,080,170 A | 6/2000 | Nash et al. |
| 6,092,526 A | 7/2000 | LaFontaine et al. |
| 6,093,166 A | 7/2000 | Knudson et al. |
| 6,093,177 A | 7/2000 | Javier, Jr. et al. |
| 6,093,185 A | 7/2000 | Ellis et al. |
| 6,102,941 A | 8/2000 | Tweden et al. |
| 6,113,630 A | 9/2000 | Vanney et al. |
| 6,113,823 A | 9/2000 | Eno |
| 6,120,520 A | 9/2000 | Saadat et al. |
| 6,123,682 A | 9/2000 | Knudson et al. |
| 6,126,649 A | 10/2000 | VanTassel et al. |
| 6,126,654 A | 10/2000 | Giba et al. |
| 6,132,451 A | 10/2000 | Payne et al. |
| 6,139,541 A | 10/2000 | Vanney et al. |
| 6,155,264 A | 12/2000 | Ressemann et al. |
| 6,156,031 A | 12/2000 | Aita et al. |
| 6,157,852 A | 12/2000 | Selmon et al. |
| 6,159,225 A | 12/2000 | Makower |
| 6,165,185 A | 12/2000 | Shennib et al. |
| 6,165,188 A | 12/2000 | Saadat et al. |
| 6,171,251 B1 | 1/2001 | Mueller et al. |
| 6,182,668 B1 | 2/2001 | Tweden et al. |
| 6,186,972 B1 | 2/2001 | Nelson et al. |
| 6,190,353 B1 | 2/2001 | Makower et al. |
| 6,193,726 B1 | 2/2001 | Vanney |
| 6,193,734 B1 | 2/2001 | Bolduc et al. |
| 6,196,230 B1 | 3/2001 | Hall et al. |
| 6,197,050 B1 | 3/2001 | Eno et al. |
| 6,197,324 B1 | 3/2001 | Crittenden |
| 6,200,311 B1 | 3/2001 | Danek et al. |
| 6,203,556 B1 | 3/2001 | Evans et al. |
| 6,213,126 B1 | 4/2001 | LaFontaine et al. |
| 6,214,041 B1 | 4/2001 | Tweden et al. |
| 6,217,527 B1 | 4/2001 | Selmon et al. |
| 6,217,549 B1 | 4/2001 | Selmon et al. |
| 6,217,575 B1 | 4/2001 | DeVore et al. |
| 6,221,049 B1 | 4/2001 | Selmon et al. |
| 6,223,752 B1 | 5/2001 | Vanney et al. |
| 6,224,584 B1 | 5/2001 | March et al. |
| 6,231,546 B1 | 5/2001 | Milo et al. |
| 6,231,551 B1 | 5/2001 | Barbut |
| 6,231,587 B1 | 5/2001 | Makower |
| 6,235,000 B1 | 5/2001 | Milo et al. |
| 6,237,607 B1 | 5/2001 | Vanney et al. |
| 6,238,406 B1 | 5/2001 | Ellis et al. |
| 6,241,667 B1 | 6/2001 | Vetter et al. |
| 6,248,112 B1 | 6/2001 | Gambale et al. |
| 6,250,305 B1 | 6/2001 | Tweden |
| 6,251,079 B1 | 6/2001 | Gambale et al. |
| 6,251,104 B1 | 6/2001 | Kesten et al. |
| 6,251,116 B1 | 6/2001 | Shennib et al. |
| 6,251,418 B1 | 6/2001 | Ahern et al. |
| 6,253,768 B1 | 7/2001 | Wilk |
| 6,253,769 B1 | 7/2001 | LaFontaine et al. |
| 6,254,564 B1 | 7/2001 | Wilk et al. |
| 6,258,052 B1 | 7/2001 | Milo |
| 6,258,119 B1 | 7/2001 | Hussein et al. |
| 6,261,304 B1 | 7/2001 | Hall et al. |
| 6,283,951 B1 | 9/2001 | Flaherty et al. |
| 6,283,983 B1 | 9/2001 | Makower et al. |
| 6,285,903 B1 | 9/2001 | Rosenthal et al. |
| 6,287,317 B1 | 9/2001 | Makower et al. |
| 6,290,709 B1 | 9/2001 | Ellis et al. |
| 6,290,728 B1 | 9/2001 | Phelps et al. |
| 6,302,875 B1 | 10/2001 | Makower et al. |
| 6,302,892 B1 | 10/2001 | Wilk |
| 6,322,548 B1 | 11/2001 | Payne et al. |
| 6,330,884 B1 | 12/2001 | Kim |
| 6,344,027 B1 | 2/2002 | Goll |
| 6,350,248 B1 | 2/2002 | Knudson et al. |
| 6,352,543 B1 | 3/2002 | Cole |
| 6,361,519 B1 | 3/2002 | Knudson et al. |
| 6,363,938 B2 | 4/2002 | Saadat et al. |
| 6,363,939 B1 | 4/2002 | Wilk |
| 6,375,615 B1 | 4/2002 | Flaherty et al. |
| 6,379,319 B1 | 4/2002 | Garibotto et al. |
| 6,387,119 B2 | 5/2002 | Wolf et al. |
| 6,390,098 B1 | 5/2002 | LaFontaine et al. |
| 6,395,208 B1 | 5/2002 | Herweck et al. |
| 6,402,740 B1 | 6/2002 | Ellis et al. |
| 6,406,488 B1 | 6/2002 | Tweden et al. |
| 6,406,491 B1 | 6/2002 | Vanney |
| 6,409,697 B2 | 6/2002 | Eno et al. |
| 6,409,751 B1 | 6/2002 | Hall et al. |
| 6,416,490 B1 | 7/2002 | Ellis et al. |
| 6,423,089 B1 | 7/2002 | Gingras et al. |
| 6,432,119 B1 | 8/2002 | Saadat |
| 6,432,126 B1 | 8/2002 | Gambale et al. |
| 6,432,127 B1 | 8/2002 | Kim et al. |
| 6,432,132 B1 | 8/2002 | Cottone et al. |
| 6,443,158 B1 | 9/2002 | LaFontaine et al. |
| 6,447,522 B2 | 9/2002 | Gambale et al. |
| 6,447,539 B1 | 9/2002 | Nelson et al. |
| 6,451,050 B1 * | 9/2002 | Rudakov et al. ............ 623/1.15 |
| 6,454,760 B2 | 9/2002 | Vanney |
| 6,454,794 B1 | 9/2002 | Knudson et al. |
| 6,458,092 B1 | 10/2002 | Gambale et al. |
| 6,458,140 B2 | 10/2002 | Akin et al. |
| 6,458,323 B1 | 10/2002 | Boekstegers |
| 6,464,709 B1 | 10/2002 | Shennib et al. |
| 6,475,226 B1 | 11/2002 | Belef et al. |
| 6,475,244 B2 | 11/2002 | Herweck et al. |
| 6,482,220 B1 | 11/2002 | Mueller |
| 6,491,689 B1 | 12/2002 | Ellis et al. |
| 6,491,707 B2 | 12/2002 | Makower et al. |
| 6,506,408 B1 | 1/2003 | Shioya |
| 6,508,783 B2 | 1/2003 | DeVore |
| 6,508,824 B1 | 1/2003 | Flaherty et al. |
| 6,508,825 B1 | 1/2003 | Selmon et al. |
| 6,511,458 B2 | 1/2003 | Milo et al. |
| 6,514,217 B1 | 2/2003 | Selmon et al. |
| 6,514,271 B2 | 2/2003 | Evans et al. |
| 6,517,527 B2 | 2/2003 | Gambale et al. |
| 6,517,558 B2 | 2/2003 | Gittings et al. |
| 6,524,323 B1 | 2/2003 | Nash et al. |

| | | |
|---|---|---|
| 6,524,324 B1 | 2/2003 | Mueller et al. |
| 6,530,914 B1 | 3/2003 | Mickley |
| 6,533,779 B2 | 3/2003 | Kinsella et al. |
| 6,537,310 B1 * | 3/2003 | Palmaz et al. ............. 623/1.13 |
| 6,544,220 B2 | 4/2003 | Shuman et al. |
| 6,544,230 B1 | 4/2003 | Flaherty |
| 6,559,132 B1 | 5/2003 | Holmer |
| 6,561,998 B1 | 5/2003 | Roth et al. |
| 6,562,066 B1 | 5/2003 | Martin |
| 6,565,528 B1 | 5/2003 | Mueller |
| 6,565,594 B1 | 5/2003 | Herweck et al. |
| 6,569,145 B1 | 5/2003 | Shmulewitz et al. |
| 6,569,147 B1 | 5/2003 | Evans et al. |
| 6,573,311 B1 | 6/2003 | Martakos et al. |
| 6,575,168 B2 | 6/2003 | LaFontaine et al. |
| 6,579,311 B1 | 6/2003 | Makower |
| 6,582,444 B2 | 6/2003 | Wilk |
| 6,582,463 B1 | 6/2003 | Mowry et al. |
| 6,585,650 B1 | 7/2003 | Solem |
| 6,587,718 B2 | 7/2003 | Talpade |
| 6,589,164 B1 | 7/2003 | Flaherty |
| 6,599,304 B1 | 7/2003 | Selmon et al. |
| 6,602,241 B2 | 8/2003 | Makower et al. |
| 6,605,053 B1 | 8/2003 | Kamm et al. |
| 6,605,113 B2 | 8/2003 | Wilk |
| 6,610,100 B2 | 8/2003 | Phelps et al. |
| 6,613,026 B1 | 9/2003 | Palasis et al. |
| 6,613,081 B2 | 9/2003 | Kim et al. |
| 6,616,626 B2 | 9/2003 | Crank et al. |
| 6,616,675 B1 | 9/2003 | Evard et al. |
| 6,632,470 B2 | 10/2003 | Morra et al. |
| 6,635,214 B2 | 10/2003 | Rapacki et al. |
| 6,638,237 B1 | 10/2003 | Guiles et al. |
| 6,638,247 B1 | 10/2003 | Selmon et al. |
| 6,638,293 B1 | 10/2003 | Makower et al. |
| 6,641,610 B2 | 11/2003 | Wolf et al. |
| 6,651,670 B2 | 11/2003 | Rapacki et al. |
| 6,652,540 B1 | 11/2003 | Cole et al. |
| 6,652,546 B1 | 11/2003 | Nash et al. |
| 6,655,386 B1 | 12/2003 | Makower et al. |
| 6,660,003 B1 | 12/2003 | DeVore et al. |
| 6,660,024 B1 | 12/2003 | Flaherty et al. |
| 6,666,863 B2 | 12/2003 | Wentzel et al. |
| 6,669,691 B1 | 12/2003 | Taimisto |
| 6,669,709 B1 | 12/2003 | Cohn et al. |
| 6,676,695 B2 | 1/2004 | Solem |
| 6,685,648 B2 | 2/2004 | Flaherty et al. |
| 6,685,716 B1 | 2/2004 | Flaherty et al. |
| 6,694,983 B2 | 2/2004 | Wolf et al. |
| 6,709,425 B2 | 3/2004 | Gambale et al. |
| 6,709,427 B1 | 3/2004 | Nash et al. |
| 6,709,444 B1 | 3/2004 | Makower |
| 6,719,770 B2 | 4/2004 | Laufer et al. |
| 6,726,677 B1 | 4/2004 | Flaherty et al. |
| 6,764,518 B2 * | 7/2004 | Godin .................... 623/23.68 |
| 2001/0000041 A1 | 3/2001 | Selmon et al. |
| 2001/0018596 A1 | 8/2001 | Selmon et al. |
| 2001/0020172 A1 | 9/2001 | Selmon et al. |
| 2001/0025643 A1 | 10/2001 | Foley |
| 2001/0027287 A1 | 10/2001 | Shmulewitz et al. |
| 2001/0034547 A1 | 10/2001 | Hall et al. |
| 2001/0037149 A1 | 11/2001 | Wilk |
| 2001/0039445 A1 | 11/2001 | Hall et al. |
| 2001/0053932 A1 | 12/2001 | Phelps et al. |
| 2002/0004662 A1 | 1/2002 | Wilk |
| 2002/0007138 A1 | 1/2002 | Wilk et al. |
| 2002/0032478 A1 | 3/2002 | Boekstegers et al. |
| 2002/0045928 A1 | 4/2002 | Boekstegers |
| 2002/0058897 A1 | 5/2002 | Renati |
| 2002/0092535 A1 | 7/2002 | Wilk |
| 2002/0095206 A1 | 7/2002 | Addonizio et al. |
| 2002/0100484 A1 | 8/2002 | Hall et al. |
| 2002/0165479 A1 | 11/2002 | Wilk |
| 2002/0165606 A1 | 11/2002 | Wolf et al. |
| 2002/0183716 A1 | 12/2002 | Herweck et al. |
| 2002/0193782 A1 | 12/2002 | Ellis et al. |
| 2003/0044315 A1 | 3/2003 | Boekstegers |
| 2003/0045828 A1 | 3/2003 | Wilk |
| 2003/0055371 A1 | 3/2003 | Wolf et al. |
| 2003/0078561 A1 | 4/2003 | Gambale et al. |
| 2003/0105514 A1 | 6/2003 | Phelps et al. |
| 2003/0120195 A1 | 6/2003 | Milo et al. |
| 2003/0149474 A1 | 8/2003 | Becker |
| 2003/0158573 A1 | 8/2003 | Gittings et al. |
| 2003/0163198 A1 | 8/2003 | Morra et al. |
| 2003/0181938 A1 | 9/2003 | Roth et al. |
| 2003/0191449 A1 | 10/2003 | Nash et al. |
| 2003/0195457 A1 | 10/2003 | LaFontaine et al. |
| 2003/0195458 A1 | 10/2003 | Phelps et al. |
| 2003/0204160 A1 | 10/2003 | Kamm et al. |
| 2003/0212413 A1 | 11/2003 | Wilk |
| 2003/0216679 A1 | 11/2003 | Wolf et al. |
| 2003/0229366 A1 | 12/2003 | Reggie et al. |
| 2003/0236542 A1 | 12/2003 | Makower |
| 2004/0006298 A1 | 1/2004 | Wilk |
| 2004/0015225 A1 | 1/2004 | Kim et al. |
| 2004/0019348 A1 | 1/2004 | Stevens et al. |
| 2004/0037946 A1 | 2/2004 | Morra et al. |
| 2004/0044392 A1 | 3/2004 | Von Oepen |
| 2004/0059280 A1 | 3/2004 | Makower et al. |
| 2004/0073157 A1 | 4/2004 | Knudson et al. |
| 2004/0073238 A1 | 4/2004 | Makower |
| 2004/0077987 A1 | 4/2004 | Rapacki et al. |
| 2004/0077988 A1 | 4/2004 | Tweden et al. |
| 2004/0077990 A1 | 4/2004 | Knudson et al. |
| 2004/0088042 A1 | 5/2004 | Kim et al. |
| 2004/0106931 A1 | 6/2004 | Guiles et al. |

FOREIGN PATENT DOCUMENTS

| | | |
|---|---|---|
| WO | WO 96/35469 | 11/1996 |
| WO | WO 96/39962 | 12/1996 |
| WO | WO 96/39964 | 12/1996 |
| WO | WO 96/39965 | 12/1996 |
| WO | WO 97/13463 | 4/1997 |
| WO | WO 97/13471 | 4/1997 |
| WO | WO 97/27893 | 8/1997 |
| WO | WO 97/27897 | 8/1997 |
| WO | WO 97/27898 | 8/1997 |
| WO | WO 97/32551 | 9/1997 |
| WO | WO 97/43961 | 11/1997 |
| WO | WO 98/03118 | 1/1998 |
| WO | WO 98/06356 | 2/1998 |
| WO | WO 98/10714 | 3/1998 |
| WO | WO 98/16161 | 4/1998 |
| WO | WO 98/24373 | 6/1998 |
| WO | WO 98/25533 | 6/1998 |
| WO | WO 98/38916 | 9/1998 |
| WO | WO 98/38925 | 9/1998 |
| WO | WO 98/38939 | 9/1998 |
| WO | WO 98/38941 | 9/1998 |
| WO | WO 98/39038 | 9/1998 |
| WO | WO 98/46115 | 10/1998 |
| WO | WO 98/46119 | 11/1998 |
| WO | WO 98/49964 | 11/1998 |
| WO | WO 98/57590 | 12/1998 |
| WO | WO 98/57591 | 12/1998 |
| WO | WO 98/57592 | 12/1998 |
| WO | WO 99/07296 | 2/1999 |
| WO | WO 99/08624 | 2/1999 |
| WO | WO 99/15220 | 4/1999 |
| WO | WO 99/17671 | 4/1999 |
| WO | WO 99/17683 | 4/1999 |

| | | |
|---|---|---|
| WO | WO 99/21490 | 5/1999 |
| WO | WO 99/21510 | 5/1999 |
| WO | WO 99/22655 | 5/1999 |
| WO | WO 99/22658 | 5/1999 |
| WO | WO 99/25273 | 5/1999 |
| WO | WO 99/27985 | 6/1999 |
| WO | WO 99/35977 | 7/1999 |
| WO | WO 99/35979 | 7/1999 |
| WO | WO 99/35980 | 7/1999 |
| WO | WO 99/36000 | 7/1999 |
| WO | WO 99/36001 | 7/1999 |
| WO | WO 99/38459 | 8/1999 |
| WO | WO 99/40853 | 8/1999 |
| WO | WO 99/40868 | 8/1999 |
| WO | WO 99/40963 | 8/1999 |
| WO | WO 99/44524 | 9/1999 |
| WO | WO 99/48545 | 9/1999 |
| WO | WO 99/48549 | 9/1999 |
| WO | WO 99/49793 | 10/1999 |
| WO | WO 99/49910 | 10/1999 |
| WO | WO 99/51162 | 10/1999 |
| WO | WO 99/53863 | 10/1999 |
| WO | WO 99/55406 | 11/1999 |
| WO | WO 99/60941 | 12/1999 |
| WO | WO 99/62430 | 12/1999 |
| WO | WO 00/09195 | 2/2000 |
| WO | WO 00/12029 | 3/2000 |
| WO | WO 00/13722 | 3/2000 |
| WO | WO 00/15146 | 3/2000 |
| WO | WO 00/15147 | 3/2000 |
| WO | WO 00/15148 | 3/2000 |
| WO | WO 00/15149 A1 | 3/2000 |
| WO | WO 00/15275 | 3/2000 |
| WO | WO 00/18302 | 4/2000 |
| WO | WO 00/18323 | 4/2000 |
| WO | WO 00/18325 | 4/2000 |
| WO | WO 00/18326 | 4/2000 |
| WO | WO 00/18331 | 4/2000 |
| WO | WO 00/18462 | 4/2000 |
| WO | WO 00/21436 | 4/2000 |
| WO | WO 00/21461 | 4/2000 |
| WO | WO 00/21463 | 4/2000 |
| WO | WO 00/24449 | 5/2000 |
| WO | WO 00/33725 | 6/2000 |
| WO | WO 00/35376 | 6/2000 |
| WO | WO 00/36997 | 6/2000 |
| WO | WO 00/41632 | 7/2000 |
| WO | WO 00/41633 | 7/2000 |
| WO | WO 00/43051 | 7/2000 |
| WO | WO 00/45711 | 8/2000 |
| WO | WO 00/45886 | 8/2000 |
| WO | WO 00/49952 | 8/2000 |
| WO | WO 00/49954 | 8/2000 |
| WO | WO 00/49956 | 8/2000 |
| WO | WO 00/54660 | 9/2000 |
| WO | WO 00/54661 | 9/2000 |
| WO | WO 00/56224 | 9/2000 |
| WO | WO 00/56225 | 9/2000 |
| WO | WO 00/56387 | 9/2000 |
| WO | WO 00/66007 | 11/2000 |
| WO | WO 00/66009 | 11/2000 |
| WO | WO 00/66035 | 11/2000 |
| WO | WO 00/69346 | 11/2000 |
| WO | WO 00/69504 | 11/2000 |
| WO | WO 00/71195 A1 | 11/2000 |
| WO | WO 01/08566 A1 | 2/2001 |
| WO | WO 01/08602 A1 | 2/2001 |
| WO | WO 01/10340 A1 | 2/2001 |
| WO | WO 01/10341 A2 | 2/2001 |
| WO | WO 01/10347 A1 | 2/2001 |
| WO | WO 01/10348 A1 | 2/2001 |
| WO | WO 01/10349 A1 | 2/2001 |
| WO | WO 01/10350 A1 | 2/2001 |
| WO | WO 01/17440 A1 | 3/2001 |
| WO | WO 01/17456 A1 | 3/2001 |
| WO | WO 01/23016 A1 | 4/2001 |
| WO | WO 01/41657 A1 | 6/2001 |
| WO | WO 01/49187 A1 | 7/2001 |
| WO | WO 01/68158 A1 | 9/2001 |
| WO | WO 01/70133 A2 | 9/2001 |
| WO | WO 01/72239 A2 | 10/2001 |
| WO | WO 01/78801 A2 | 10/2001 |
| WO | WO 01/82803 A1 | 11/2001 |
| WO | WO 01/82837 A2 | 11/2001 |
| WO | WO 02/011647 A2 | 2/2002 |
| WO | WO 02/011807 A2 | 2/2002 |
| WO | WO 02/013698 A1 | 2/2002 |
| WO | WO 02/013699 A1 | 2/2002 |
| WO | WO 02/013703 A1 | 2/2002 |
| WO | WO 02/013704 A1 | 2/2002 |
| WO | WO 02/024108 A2 | 3/2002 |
| WO | WO 02/024247 A1 | 3/2002 |
| WO | WO 02/024248 A1 | 3/2002 |
| WO | WO 02/026310 A1 | 4/2002 |
| WO | WO 02/026462 A1 | 4/2002 |
| WO | WO 02/030325 A2 | 4/2002 |
| WO | WO 02/030326 A2 | 4/2002 |
| WO | WO 02/030330 A2 | 4/2002 |
| WO | WO 02/032330 A2 | 4/2002 |
| WO | WO 02/034323 A2 | 5/2002 |
| WO | WO 02/045598 A2 | 6/2002 |
| WO | WO 02/049465 A2 | 6/2002 |
| WO | WO 02/056937 A2 | 7/2002 |
| WO | WO 02/058567 A2 | 8/2002 |
| WO | WO 02/058591 A2 | 8/2002 |
| WO | WO 02/060509 A1 | 8/2002 |
| WO | WO 02/062265 A2 | 8/2002 |
| WO | WO 02/064020 A2 | 8/2002 |
| WO | WO 02/071974 A2 | 9/2002 |
| WO | WO 02/074175 A2 | 9/2002 |
| WO | WO 02/091958 A1 | 11/2002 |
| WO | WO 03/008005 A2 | 1/2003 |
| WO | WO 03/015638 A2 | 2/2003 |
| WO | WO 03/017870 A1 | 3/2003 |
| WO | WO 03/024307 A2 | 3/2003 |
| WO | WO 03/028522 A2 | 4/2003 |
| WO | WO 03/030744 A1 | 4/2003 |
| WO | WO 03/030784 A1 | 4/2003 |
| WO | WO 03/041469 A2 | 6/2003 |

OTHER PUBLICATIONS

Wakabayashi et al.; *Myocardial boring for the ischemic heart*; International Cardiovascular Society; vol. 95 (Nov. 1967) pp. 743–752.

Larry et al.; *Myocardial revascularization experiments using the epicardium*; Arch. Surg., vol. 98 (Jan. 1969) pp. 69–72.

Kuzela et al.; *Experimental evaluation of direct transventricular revascularization*; Journal of Thoracic and Cardiovascular Surgery, vol. 57 (Jan.–Jun. 1969) pp. 770–773.

Anabtawi et al.; *Experimental evaluation of myocardial tunnelization as a method of myocardial revascularization*; Journal of Thoracic and Cardiovascular Surgery, (Nov. 1969) pp. 638–646.

Palmaz et al.; *Expandable intrahepatic portacaval shunt stents in dogs with chronic portal hypertension*; AJR, vol. 147 (Dec. 1986) pp. 1251–1254.

Palmaz et al.; *Expandable intrahepatic portacaval shunt stents: early experience in the dog*; AJR, vol. 145 (Oct. 1985) pp. 821–825.

Gardner et al.; *An experimental anatomic study of indirect myocardial revascularization*; Journal of Surgical Research, vol. 11 (1971) pp. 243–247.

Lary et al., *A method for creating a coronary–myocardial artery*; Surgery, vol. 59 (Jun. 1966) pp. 1061–10640.

Ahmed et al.; *Silent left coronary artery–cameral fistula: probable cause of myocardial ischemia*; American Heart Journal, vol. 104 (Oct. 1982) pp. 869–870.

Zemel et al.; *Percutaneous transjugular portosystemic shunt*; JAMA, vol. 266 (Jul. 1991) pp. 390–393.

Richter et al.; *Transjugular intrahepatic poracaval stent shunt: preliminary clinical results*; RSNA–SCVIR, vol. 174 (Mar. 1990) pp. 1027–1030.

Angell et al., *Organ viability with hypothermia*, The Journal of Thoracic and Cardiovascular Surgery, vol. 58, No. 5 (Nov. 1969), pp. 619–646.

Massimo et al., Myocardial, *Revasuclarization by a New Method of Carrying Blood Directly from the left ventricular cavity into the Coronary Circulation*, from the S. Maria.Nuova Hospital: Surgeon–in–Chief, Tominiaso Greco, M.D., received for publication Oct. 16, 1956, J. Thoracic Surgery vol. 34: (1957) pp. 257–264.

Archie, Joseph P. Jr., *Intramyocardial Pressure: Effect of Preload on Transmural Distribution of Systolic Coronary Blood Flow*, The American Journal of Cardiology, vol. 35, (Jun. 1975), pp. 904–911.

Burch, et al., An International Publication for the Study of the Circulation, American Heart Journal, (Jan. 1980), pp. 8–9.

Lee et al., *Effects of laser irradiation delivered by flexible fiberoptic system on the left ventricular internal myocardium*, AMJ, (Sep. 1983), vol. 106, No. 3, pp. 587–590.

Galioto, et la., *Right Coronary artery to left ventricle fistula*, AHJ, vol. 82, No. 1, (Jul. 1971), No. 1, p. 93–97.

Levinsky, et al., *The Revival of the Horseshoe Graft*, The Thoracic and Cardiovascular Surgeon, vol. 27, No. 5, (Oct. 1979), pp. 281–344.

Medical Industry Today Headline News, Device and Diagnostics, (Jul. 17, 1998), Article #07179802, Article is 349 words long, pp. 1–2.

Medical Industry Today Headline News, Financial News, (Jul. 17, 1998), Article #07179808, article is 560 words long, pp. 1–2.

Munro, et al., *The possibility of myocardial revascularization by creation of a left ventriculocoronary artery fistula*, The Journal of Thoracic and Cardiovascular Surgery, vol. 58, (1969), pp. 25–32.

Bohning, et al., *The Thebesian Vessels as a Source of Nourishment for the Myocardium*, From the Cardiovascular Laboratory, Department of Physiology, Michael Reese Hospital, Chicago, Received for publication on Jun. 23, 1933.

Oesterle, et al., *Catheter–Based Coronary Bypass: A Development Update*, Catheterization and Cardiovascular Interventions, vol. 58, (2003), pp. 212–218.

Goldman, et al., *Experimental Methods for Producing a Collateral Circulation to the Heart Directly from the Left Ventricle*, J. Thoracic Surgery, vol. 31, No. 3 (Mar. 1956) pp. 364–374.

Cohen et al., *Alternative Approaches to Coronary Revascularization*, Current International Cardiology Reports, vol. 1 (1999), pp. 138–146.

* cited by examiner

ENCASED IMPLANT AND METHODS

TECHNICAL FIELD

This disclosure relates to vascular implants, methods of making, and methods of using.

BACKGROUND

U.S. Pat. No. 5,944,019, issued Aug. 31, 1999, teaches an implant for defining a blood flow conduit directly from a chamber of the heart to a lumen of a coronary vessel. An embodiment disclosed in this patent teaches an L-shaped implant in the form of a rigid conduit having one leg sized to be received within a lumen of a coronary artery and a second leg sized to pass through the myocardium and extend into the left ventricle of the heart. As disclosed in the '019 patent, the conduit is rigid and remains open for blood flow to pass through the conduit during both systole and diastole. The conduit penetrates into the left ventricle in order to prevent tissue growth and occlusions over an opening of the conduit. U.S. Pat. No. 5,944,019 is incorporated by reference herein.

U.S. Pat. No. 5,984,956, issued Nov. 16, 1999, discloses an implant with an enhanced fixation structure. The enhanced fixation structure includes a fabric surrounding at least a portion of the conduit to facilitate tissue growth on the exterior of the implant. U.S. Pat. No. 5,984,956 is incorporated herein by reference. U.S. Pat. No. 6,029,672 issued Feb. 29, 2000 teaches procedures and tools for placing a conduit. U.S. Pat. No. 6,029,672 is incorporated herein by reference.

Improvements in implants continue to be desirable.

SUMMARY

In one aspect, a vascular implant is provided that includes a scaffold and a tubing in covering relation to the scaffold. Preferably, the scaffold completely embeds the scaffold.

In another aspect, a method of making a vascular implant is provided. The method includes completely covering a scaffold interior surface and exterior surface with a tubing.

In another aspect, a method for performing a coronary vessel bypass procedure is provided. The method includes forming a blood flow path from a heart chamber directly to a coronary vessel by placing a conduit in a heart wall between the chamber and the vessel. The conduit includes tubing completely lining both an interior surface of the conduit and an exterior surface of the conduit.

DETAILED DESCRIPTION

Figure 1:
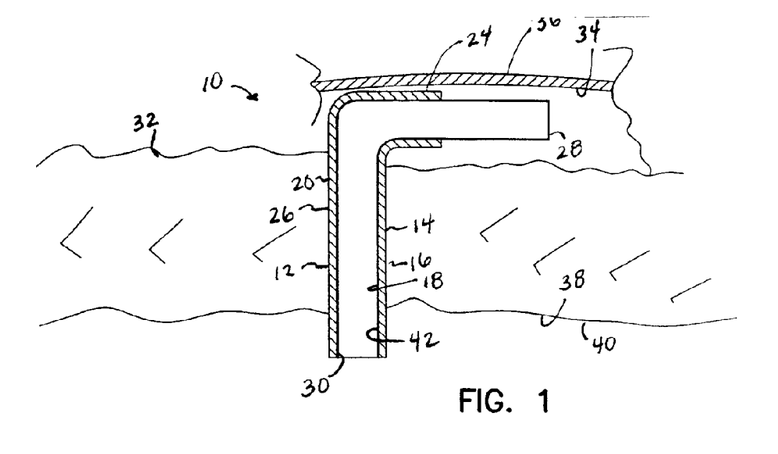
FIG. 1 is a side sectional view of one embodiment of an implant shown in place in a human heart wall with the implant establishing a direct blood flow path from a heart chamber to a coronary vessel, constructed according to principles of this disclosure.

With initial reference to FIG. 1, an implant is shown generally at 10. The implant 10 includes a composite of a hollow, rigid conduit 12. The conduit 12 includes a wall 14 defining an outer surface 16 and a hollow interior 18. In preferred embodiments, the wall 14 has a circular cross-section, forming a tube or cylinder 20. The conduit 12 includes a first portion 24, preferably corresponding to a vessel or vasculature portion, and a second portion 26, generally corresponding to a myocardial portion. The conduit 12 includes an open first end 28 that is defined by the vascular portion 24. The conduit 12 also includes an open second end 30 that is defined by the myocardial portion 26.

In FIG. 1, a cross-section of the myocardium 32 of a human heart is shown. As can be seen in FIG. 1, in preferred embodiments, the first portion 24 is dimensioned to be received within a lumen 34 of a coronary vasculature 36. As used herein, the term "vasculature" refers to veins or arteries. Note that the vasculature 36 resides exterior of the myocardium 32. The second portion 26 is dimensioned to extend from the vasculature 36 through the myocardium 32 and into a heart chamber 38. In preferred implementations, the heart chamber 38 will be the left ventricle 40. As can be seen in FIG. 1, the conduit 12 defines a blood flow pathway 42 within the interior 18 between the open first end 28 and the open second end 30. This allows for the flow of oxygenated blood directly from the left ventricle 40 through the pathway 42 and into the vasculature 36.

Figures 4, 5:
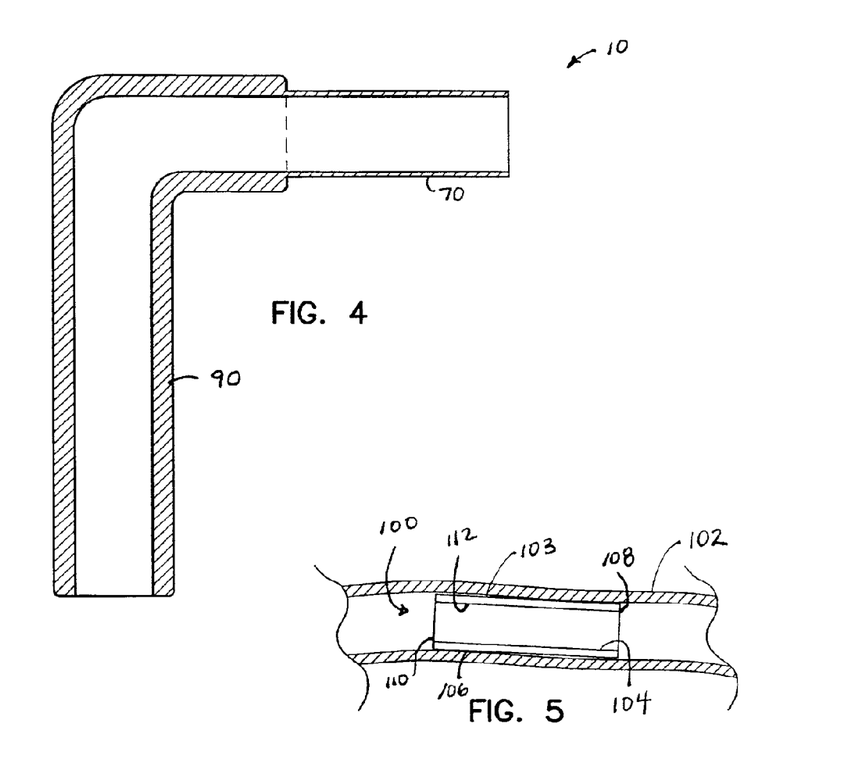
FIG. 4 is a cross-sectional view of the implant shown in FIGS. 2 and 3 in another step of making the implant.
FIG. 5 is a side sectional view of a second embodiment of an implant shown in place in a human blood vessel, constructed according to principles of this disclosure.

Turning now to FIG. 4, the implant 10 is illustrated enlarged and in cross-section. The implant 10 is shown as it would appear before being operably inserted in the environment shown in FIG. 1. In reference now to FIG. 2, in preferred embodiments, the implant 10 includes a scaffold 50 to provide framework or support overall to the implant 10. The scaffold 50 is generally made from a material that will provide strength and integrity to the overall implant 10 and with which will be able to withstand the muscular pressure exerted by systolic and diastolic contractions of the myocardium 32. The scaffold 50 may either be impermeable or permeable. Suitable materials for the scaffold 50 include titanium or stainless steel. If the scaffold 50 is designed to be permeable, the scaffold 50 is formed into a matrix such as a permeable mesh.

Figures 2, 3:
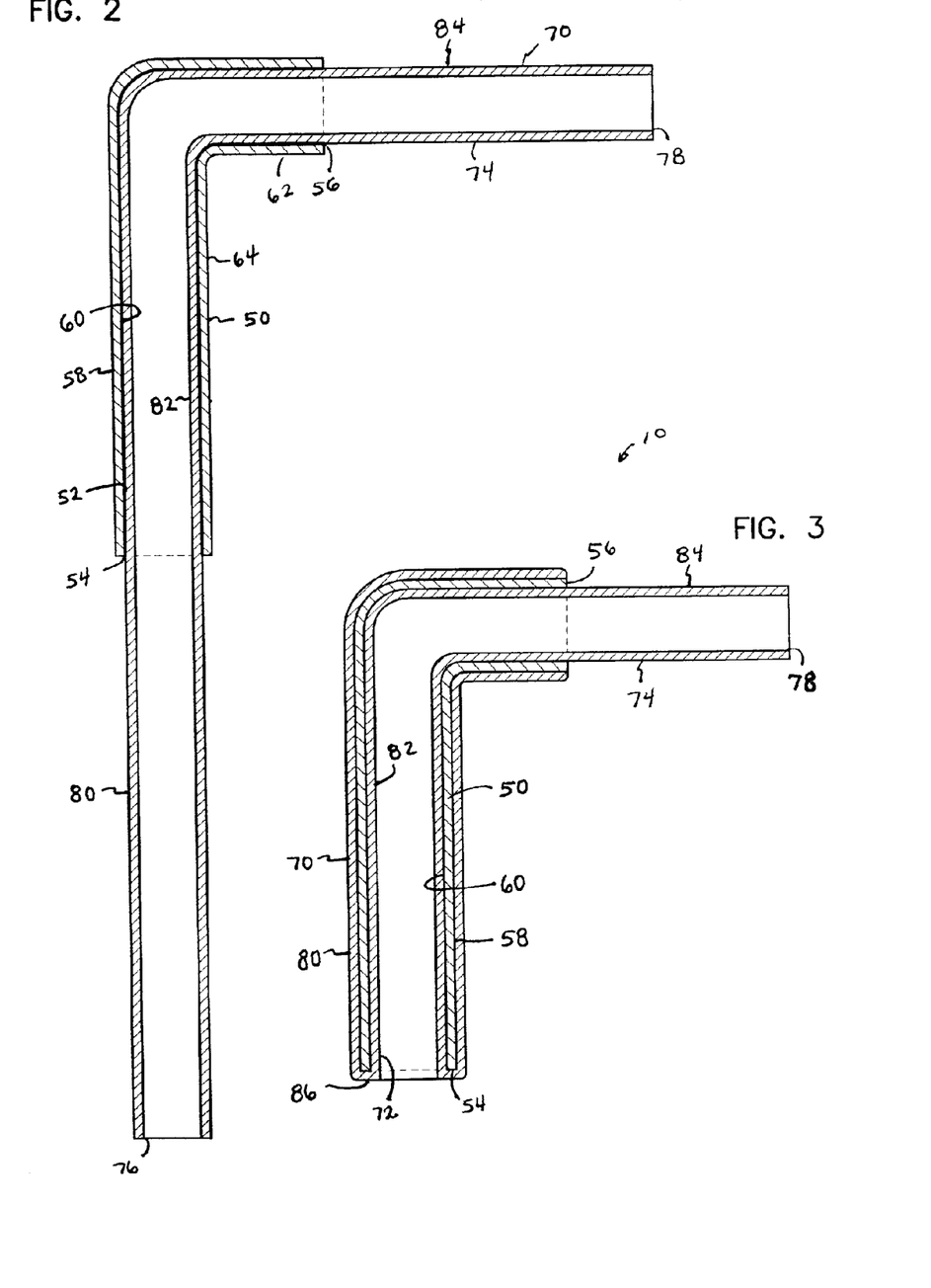
FIG. 2 is a cross-sectional view of the embodiment of the implant shown in FIG. 1 in one step of constructing the implant.
FIG. 3 is a cross-sectional view of the implant shown in FIG. 2 during another step of making the implant.

In the embodiment shown in FIG. 2, the scaffold 50 defines an interior volume 52, a first end 54 and an opposite, second end 56. The scaffold 50 also defines an exterior surface 58 and an opposite, interior surface 60. As can be seen in FIG. 2, the interior surface 60 is immediately adjacent to and lines the interior volume 52. In the particular embodiment shown in FIG. 2, the scaffold 50 is non-straight. In particular, the scaffold 50 defines an interior angle between a first portion 62 and a second portion 64. In the embodiment shown, the angle between the first portion 62 and the second portion 64 is between 80°–100°, inclusive, preferably 90°. As such, the scaffold 50 is L-shaped.

In reference now to FIG. 3, the scaffold 50 is shown with a tubing 70 in covering relation to the scaffold 50. As can be seen in FIG. 3, the scaffold interior surface 60 is completely covered by the tubing 70 from the scaffold first end 54 all the way to the scaffold second end 56. Together, the scaffold interior surface 60 and the tubing 70 define a lumen 72. The lumen 72 corresponds to the interior 18 of the finished implant 10. The lumen 72 also forms at least a part of the blood pathway 42 (FIG. 1).

Still in reference to FIG. 3, the scaffold exterior surface 58 is also completely covered by the tubing 70 from the scaffold first end 54 to the scaffold second end 56. In this context, by "completely covered", it is meant that the tubing 70 is continuous and without apertures, openings, passages, slits, slots, or other voids such that it forms a complete blanket over the scaffold 50 protecting the scaffold 50 from any exposures. From a review of FIG. 3, it can be seen that the tubing 70 completely encases the scaffold 50 to provide protection, durability, strength, and vascular compatibility to the scaffold 50. In preferred embodiments, the tubing 70 is made from expanded polytetrafluoroethylene (ePTFE).

FIGS. 2–4 illustrate example steps that may be followed to construct the implant 10. In FIG. 2, the tubing 70 is shown extended through the interior volume 52 of the scaffold 50. One way of accomplishing this step is by providing the scaffold 50 and inserting the tubing 70 through the interior volume 52 of the scaffold 50.

In general, the tubing 70 includes a wall 74 having a circular cross-section, such that the tubing 70 is generally cylindrical in shape. The tubing 70 includes an open first end 76, and an opposite, open second end 78. As can be seen in FIG. 2, the tubing 70 can be divided into three sections: a first section 80, a second section 82, and a third section 84. The first section 80 is a portion of the tubing that, during this step of the construction process in FIG. 2, extends from the first end 54 of the scaffold 50 exterior of the scaffold 50 in this step (but it is in subsequent steps, FIG. 3). That is, the first section 80 is not in contact with the scaffold 50. The second section 82 extends between the first section 80 and the third section 84. The second section 82 is the portion of the tubing 70 that is adjacent to and in contact with the scaffold 50 between the first end 54 and the second end 56. In the construction step shown in FIG. 2, the second section 82 extends along the interior surface 60 of the scaffold 50. The third section 84 projects from the second end 56 of the scaffold 50. The third section 84 is not in contact with the scaffold 50. The third section 84 defines the open second end 78, while the first section 80 defines the first open end 76.

FIG. 3 shows another step for constructing the implant 10. In FIG. 3, the tubing 70 can be seen to include at least a first fold 86 covering the scaffold first end 54. This may be accomplished by folding the first section 80 of the tubing 70 back against itself around the first end 54 and to cover the exterior surface 58 of the scaffold 50. In the particular embodiment shown, the first end 76 of the tubing 70 is adjacent to and against the scaffold second end 56. As can be seen in FIG. 3, the third section 84 remains in the same form that it was in FIG. 2, that is, extending from the scaffold second end 56, with the tubing second end 78 being remote from the scaffold 50.

Next, the tubing 70 and the scaffold 50 are bonded together to form a composite 90. The bonding may be done in a variety of methods including mechanical bonding, chemical bonding, and thermal bonding. FIG. 4 illustrates the resulting implant 10 after the tubing 70 and the scaffold 50 have been bonded together. The resulting implant 10 in FIG. 4 is the same implant shown in FIG. 1.

Reference is now made to FIGS. 5–9. FIG. 5 illustrates another embodiment of an implant 100. The implant 100 is shown within a blood vessel 102. The blood vessel 102 can be a coronary vessel or any of the vessels in the lumen body. The implant 100 can be used to extend through the myocardium of a human heart, as described above in connection with the embodiment of FIG. 1. The implant 100 functions as a stent 103 to help insure the passage of blood through a pathway 104. In the one shown in FIG. 5, the implant 100 is cylindrical in shape having a wall 106, opposite first and second ends 108, 110, and an interior volume 112. The interior volume 112 forms a portion of the blood pathway 104.

Figure 6:
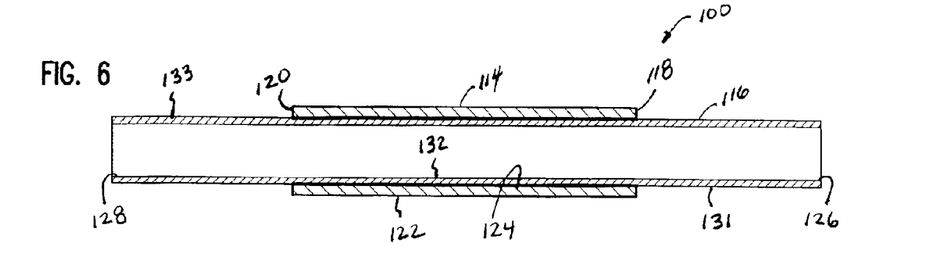
FIG. 6 is a cross-sectional view of the embodiment of the implant shown in FIG. 5 during one step of constructing the implant.
Figure 7:
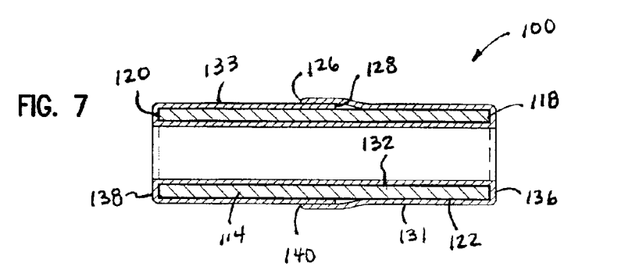
FIG. 7 is a cross-sectional view of the implant shown in FIG. 6, during another step of constructing the implant.
Figure 8:
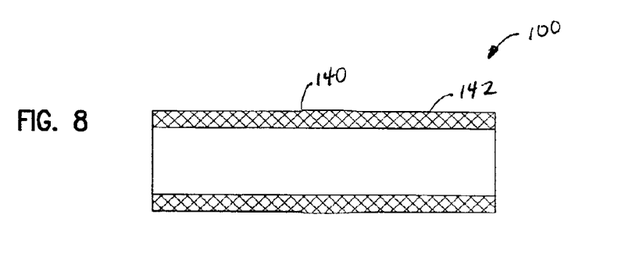
FIG. 8 is a cross-sectional view of the implant shown in FIGS. 6 and 7 during another step for constructing the implant.

FIGS. 6–8 show steps in constructing the implant 100. As with the embodiment of FIGS. 1–4, the implant 100 includes a scaffold 114 and tubing 116. The scaffold 114, in this embodiment, is straight and unbent. The scaffold 114 defines first and second opposite ends 118, 120, an exterior surface 122, and an opposite interior surface 124.

Still in reference to FIG. 6, the tubing 116 has an open first end 126 and an opposite second end 128. The tubing 116 can be divided into first, second, and third sections 131, 132, and 133, respectively. The first section 131 extends from the first end 118 of the scaffold 114 and is not in immediate contact with the scaffold 114 in FIG. 6. The second section 132 is the portion of the tubing 116 that is in contact with the scaffold 114. The second section 132 extends between the first and second ends 118, 120 and lines the interior surface 124 of the scaffold 114. The third section 133 extends from the scaffold 114 from the second end 120 and does not immediately contact the scaffold 114 in the FIG. 6 illustration.

FIG. 7 illustrates a second step in forming the implant 100. In FIG. 7, the implant 100 is shown after the first section 131 has been folded around the first end 118 of the scaffold 114 to form a first fold 136 in the tubing 116. Also shown in FIG. 7, the third section 133 has been folded around the second end 120 of the scaffold 114 to form a second fold 138 in the tubing 116. As can be appreciated by reviewing FIG. 7, the tubing 116 is folded back around each of the ends 118, 120 such that the tubing 116 completely encases the scaffold 114. That is, the first section 131 is folded around the first end 118 to cover the exterior surface 122, as the third section 133 is folded around the second end 120 to also cover the exterior surface 122. The first end 126 of the tubing 116 meets up with the second end 128 of the tubing 116 in a manner in which the ends 126, 128 either abut each other or overlap to form a seam or joint 140. The joint 140 can be along any portion of the scaffold 114. In the particular embodiment shown in FIG. 7, the joint 140 is at about the mid point between the first and second ends 118, 120 of the scaffold 114.

FIG. 8 illustrates the implant 100 after the tubing 116 and scaffold 114 are bonded to form bonded structure 142. As with the implant 10, the implant 100 may be formed by one or combinations of mechanical bonding, chemical bonding, and thermal bonding.

Figure 9:
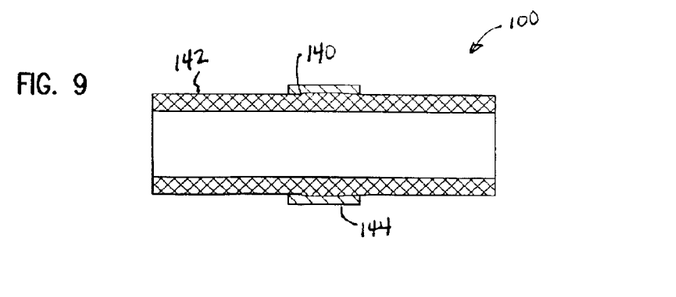
FIG. 9 is a cross-sectional view of the implant shown in FIGS. 6–8 and including an optional cuff.

The implant 100 can include an optional sleeve or cuff 144 around the joint 140 containing a tissue integration material, such as tissue growth inducing substances. This is described in commonly assigned U.S. Pat. No. 5,984,956, which is incorporated by reference herein.

Figure 10:
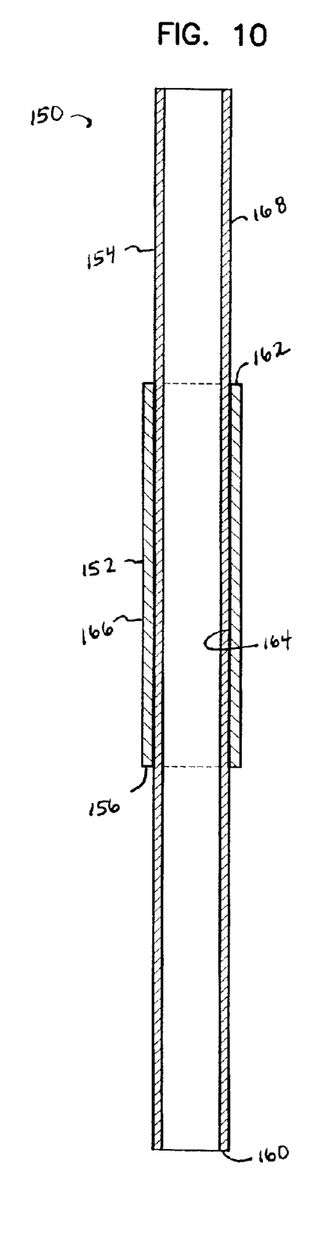
FIG. 10 is a cross-sectional view of another embodiment of an implant shown during one step for constructing the implant.
Figure 11:
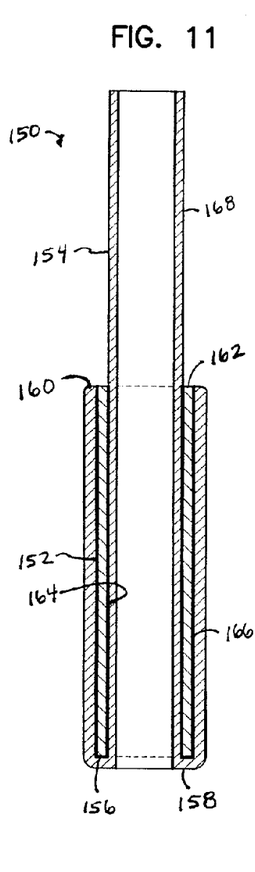
FIG. 11 is a cross-sectional view of the implant shown in FIG. 10, during another step for constructing the implant.
Figure 12:
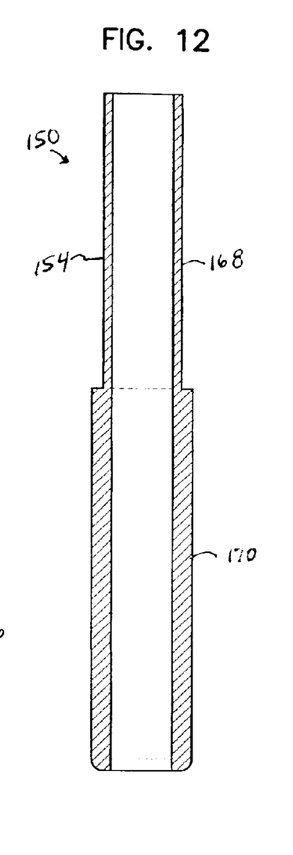
FIG. 12 is a cross-sectional view of the implant shown in FIGS. 10 and 11 in a final step for constructing the implant.

Attention is next directed to the embodiment of FIGS. 10-12. An implant 150 is shown in FIG. 12, with steps in constructing the implant 150 shown in FIGS. 10 and 11. The implant 150 is analogous to the implant 10 of FIGS. 1-4 with the exception that the implant 150 is straight and unbent. The implant 150 is not L-shaped as the implant 10.

Other than the lack of an angle, the implant 150 is the same as the implant 10. As such, the implant 150 includes a scaffold 152 and tubing 154. The tubing 154 is bent around a first end 156 of the scaffold 152 to form a fold 158 adjacent to and against the first end 156. The tubing 154 is folded over the scaffold 152 such that the first end 160 of the tubing 154 is adjacent to and against the second end 162 of the scaffold 152. In this manner, the tubing 154 completely encases the scaffold 152 by completely lining the interior surface 164 of the scaffold 152 and covering the exterior surface 166 of the scaffold 152. A second section 168 of the tubing 154 remains extending from the second end 162 and is out of immediate and adjacent contact with the scaffold 152. FIG. 12 shows the implant 150 after the scaffold 152 and tubing 154 are bonded to form a bonded implant structure 170. Again, the bonding can be done by one of, or combinations of, mechanical, chemical, and thermal bonding.

From a review of each of the embodiments in FIGS. 1–12, it should be appreciated that the implants formed have scaffolds that are completely encased and covered by tubing. In preferred embodiments, there is no portion of the scaffold wall (including interior surface, exterior surface, and end rims) that is left exposed—all of these portions are covered by the tubing.

The implants 10, 100, and 150 can be used to treat human patients. In one application, the implant can be used in a method for performing a coronary vessel bypass procedure. This method includes forming a blood flow path, such as pathway 42 from heart chamber 38 directly to the coronary vessel 36 at a site in the vessel positioned between an obstruction in the vessel and tissue of the heart to be supplied with blood by the vessel. This step includes placing the implant 10, 100, 150 in the heart wall 32 between the chamber 38 and the vessel 36 with one end of the implant 10, 100, 150 protruding into the chamber 38 beyond an interior surface of the heart wall 32. The method includes the implant having tubing completely lining an interior surface and completely lining an exterior surface between opposite ends of the implant.

Methods for treating human patients also may include forming a blood path in a blood vessel by positioning an implant in the vessel. The implant would include implants of the type described herein.

The above description represents a complete description of example embodiments incorporating principles of the inventions. Many embodiments can be made.

What is claimed is:

1. A vascular implant comprising:
   (a) a scaffold defining an interior volume, a first end, and an opposite second end; said scaffold having an exterior surface and an interior surface, said scaffold interior surface defining a lumen, said lumen including a longitudinal axis, said longitudinal axis including a bend between said first end and said second end;
      (i) said interior surface lining said interior volume; and
   (b) a tubing in covering relation to said scaffold;
      (i) said scaffold interior surface being completely covered by said tubing from said first end to said second end;
      (ii) said scaffold exterior surface being completely covered by said tubing from said first end to said second end,
   wherein said tubing includes a portion in extension away from and/or remote from said scaffold,
   wherein said tubing is folded over one of said first and second ends of the scaffold.

2. A vascular implant according to claim 1 wherein:
   (a) said tubing comprises first and second ends and at least a first fold;
      (i) said first fold covering said scaffold first end.

3. A vascular implant according to claim 2 wherein:
   (a) said tubing first end is adjacent to and against said scaffold second end.

4. A vascular implant according to claim 1 wherein:
   (a) said tubing includes a first end and a second end;
      (i) said tubing second end forming an end of said extension remote from said scaffold.

5. A vascular implant according to claim 4 wherein:
   (a) said scaffold is L-shaped.

6. A vascular implant according to claim 1 wherein:
   (a) said tubing comprises expanded polytetrafluoroethylene.

7. A vascular implant according to claim 1 wherein:
   (a) said scaffold comprises titanium or stainless steel.

8. A vascular implant according to claim 1 wherein:
   (a) said scaffold comprises an impermeable tube.

9. A vascular implant according to claim 1 wherein:
   (a) said scaffold comprises an impermeable mesh.

10. A method of making a vascular implant; the method comprising:
    (a) providing a tubing having first and second ends;
    (b) providing a scaffold having an exterior surface; an interior surface; an interior volume; a scaffold first end; and an opposite scaffold second end, said scaffold interior surface defining a lumen, said lumen including a longitudinal axis, said longitudinal axis including a bend between said scaffold first end and said scaffold second end;
    (c) completely covering the scaffold interior surface from the scaffold first end to the scaffold second end with the tubing; and
    (d) completely covering the scaffold exterior surface from the scaffold first end to the scaffold second end with the tubing;
    wherein the vascular implant includes a portion of the tubing in extension away from and/or remote from said scaffold;
    wherein said tubing is folded over one of said first and second ends of the scaffold.

11. A method according to claim 10 further including:
    (a) after said step of providing a scaffold, inserting the tubing through the interior volume of the scaffold; and
    (b) folding the tubing over at least the first end of the scaffold from the interior surface of the scaffold to the exterior surface of the scaffold.

12. A method according to claim 11 further including:
    (a) after said step of folding, securing the tubing to the scaffold.

13. A method according to 12 wherein:
(a) said step of securing includes securing the tubing first end adjacent to and against the scaffold second end on the exterior surface of the scaffold.

14. A method according to claim 10 wherein:
(a) said tubing includes a first end and a second end;
(b) said step of inserting the tubing includes inserting only a portion of the tubing into the scaffold interior volume and leaving a remaining portion of the tubing in extension from the scaffold;
  (i) the tubing second end forming an end of the remaining portion remote from the scaffold.

15. A method according to claim 14 wherein:
(a) said step of providing a scaffold includes providing an L-shaped scaffold.

16. A method according to claim 10 further including:
(a) securing the tubing to the scaffold by bonding; the bonding including at least one of mechanical bond, chemical bond, and thermal bond.

17. A method for performing a coronary vessel bypass procedure for supplementing a flow of blood to a coronary vessel; the method comprising:

(a) forming a blood flow path from a heart chamber directly to the coronary vessel at a site in the vessel positioned between an obstruction in the vessel and tissue of the heart to be supplied with blood by the vessel;
  (i) the step of forming including placing a conduit in a heart wall between the chamber and the vessel with a first end of the conduit protruding into the chamber and protruding beyond an interior surface of the heart wall; the conduit having a second end;
    (A) the conduit including a tubing completely lining an interior surface of the conduit between the first and second ends, and completely lining an exterior surface of the conduit between the first and second ends, said interior surface of the conduit defining a lumen, said lumen including a longitudinal axis, said longitudinal axis including a bend between said first end and said second end,
    wherein said tubing includes a portion in extension away from and/or remote from said conduit wherein said tubing is folded over one of said first and second ends of the conduit.

* * * * *

UNITED STATES PATENT AND TRADEMARK OFFICE
CERTIFICATE OF CORRECTION

PATENT NO. : 6,949,118 B2
DATED : September 27, 2005
INVENTOR(S) : Robert Kohler et al.

Page 1 of 1

It is certified that error appears in the above-identified patent and that said Letters Patent is hereby corrected as shown below:

Column 6,
Line 35, "an impermeable" should read -- a permeable --.

Signed and Sealed this

Twenty-second Day of November, 2005

JON W. DUDAS
*Director of the United States Patent and Trademark Office*